United States Patent
Catching et al.

(10) Patent No.: US 9,945,790 B2
(45) Date of Patent: Apr. 17, 2018

(54) IN-SITU SPECTRAL PROCESS MONITORING

(71) Applicant: Viavi Solutions Inc., Milpitas, CA (US)

(72) Inventors: Benjamin F. Catching, Santa Rosa, CA (US); Marc K. Von Gunten, Los Altos, CA (US); Curtis R. Hruska, Cloverdale, CA (US); Paula Smith, Santa Rosa, CA (US); Paul G. Coombs, Santa Rosa, CA (US)

(73) Assignee: VIAVI Solutions Inc., San Jose, CA (US)

( * ) Notice: Subject to any disclaimer, the term of this patent is extended or adjusted under 35 U.S.C. 154(b) by 203 days.

(21) Appl. No.: 14/819,179

(22) Filed: Aug. 5, 2015

(65) Prior Publication Data

US 2017/0038305 A1 Feb. 9, 2017

(51) Int. Cl.
*G01N 21/85* (2006.01)
*G01J 3/02* (2006.01)
*G01J 3/12* (2006.01)
*G01N 21/27* (2006.01)

(52) U.S. Cl.
CPC ............ *G01N 21/85* (2013.01); *G01J 3/0289* (2013.01); *G01J 3/0291* (2013.01); *G01J 3/12* (2013.01); *G01N 21/27* (2013.01); *G01N 21/8507* (2013.01); *G01J 2003/123* (2013.01); *G01J 2003/1234* (2013.01);
(Continued)

(58) Field of Classification Search
CPC ....................................................... G01N 21/85
USPC .......................................................... 356/416
See application file for complete search history.

(56) References Cited

U.S. PATENT DOCUMENTS

| 4,389,096 A | 6/1983 | Hori et al. |
| 4,590,466 A | 5/1986 | Wiklund et al. |
| 5,011,279 A | 4/1991 | Auweter et al. |

(Continued)

FOREIGN PATENT DOCUMENTS

| CN | 103 278 861 A | 9/2013 |
| EP | 0 491 131 A1 | 10/1991 |

(Continued)

OTHER PUBLICATIONS

Partial European Search Report corresponding to EP 16182511.2, dated Jan. 3, 2017, 7 pages.

(Continued)

*Primary Examiner* — Tarifur Chowdhury
*Assistant Examiner* — Omar Nixon
(74) *Attorney, Agent, or Firm* — Harrity & Harrity, LLP

(57) ABSTRACT

Increasing the precision of process monitoring may be improved if the sensors take the form of travelling probes riding along with the flowing materials in the manufacturing process rather than sample only when the process moves passed the sensors fixed location. The probe includes an outer housing hermetically sealed from the flowing materials, and a light source for transmitting light through a window in the housing onto the flowing materials. A spatially variable optical filter (SVF) captures light returning from the flowing materials, and separates the captured light into a spectrum of constituent wavelength signals for transmission to a detector array, which provides a power reading for each constituent wavelength signal.

27 Claims, 9 Drawing Sheets

(52) U.S. Cl.
CPC . *G01N 2201/061* (2013.01); *G01N 2201/062* (2013.01); *G01N 2201/068* (2013.01)

(56) References Cited

U.S. PATENT DOCUMENTS

| | | | |
|---|---|---|---|
| 5,949,082 A | 9/1999 | Schubert et al. | |
| 6,075,611 A * | 6/2000 | Dussan, V | G01F 1/7086 356/432 |
| 6,700,690 B1 | 3/2004 | Buchsbaum et al. | |
| 6,836,325 B2 * | 12/2004 | MacZura | G01J 3/02 356/328 |
| 6,844,930 B2 | 1/2005 | Kobayashi et al. | |
| 7,460,247 B1 | 12/2008 | Ackerman | |
| 7,907,282 B2 | 3/2011 | Coates | |
| 8,159,668 B2 | 4/2012 | Malinen et al. | |
| 9,625,628 B2 | 4/2017 | Hruska et al. | |
| 2001/0028458 A1 | 10/2001 | Xiao | |
| 2001/0055116 A1 * | 12/2001 | MacZura | G01J 3/02 356/326 |
| 2002/0039186 A1 * | 4/2002 | Rosenberg | G01J 3/02 356/432 |
| 2004/0004551 A1 * | 1/2004 | Early | G01F 23/76 340/603 |
| 2004/0054248 A1 * | 3/2004 | Kimchy | A61B 5/055 600/3 |
| 2004/0218175 A1 * | 11/2004 | Barkhoudarian | F02K 9/96 356/326 |
| 2005/0036145 A1 | 2/2005 | Meada | |
| 2005/0117156 A1 * | 6/2005 | Siepmann | G01N 21/15 356/436 |
| 2005/0213092 A1 | 9/2005 | MacKinnon et al. | |
| 2006/0175547 A1 | 8/2006 | DiFoggio | |
| 2007/0068242 A1 | 3/2007 | DiFoggio | |
| 2010/0140373 A1 * | 6/2010 | Myhre | F23M 11/045 239/71 |
| 2012/0020185 A1 * | 1/2012 | Welker | G01V 1/3843 367/16 |
| 2013/0161544 A1 * | 6/2013 | Ohnishi | G01N 21/85 250/564 |
| 2014/0320858 A1 | 10/2014 | Goldring et al. | |
| 2015/0153156 A1 | 6/2015 | Shah | |
| 2015/0219484 A1 | 8/2015 | Hruska et al. | |
| 2015/0291993 A1 * | 10/2015 | Vela | C12Q 1/06 210/745 |
| 2017/0219430 A1 | 8/2017 | Hruska et al. | |
| 2017/0038255 A1 | 9/2017 | Smith et al. | |

FOREIGN PATENT DOCUMENTS

| | | |
|---|---|---|
| EP | 0 295 546 A2 | 12/1998 |
| EP | 2600126 A2 | 6/2013 |
| JP | S5760231 A | 4/1982 |
| JP | S5922189 A | 2/1984 |
| JP | 2003510560 A | 3/2003 |
| JP | 2005043092 A | 2/2005 |
| JP | 2005517175 A | 6/2005 |
| JP | 2005526332 A | 9/2005 |
| JP | 2009520205 A | 5/2009 |
| JP | 2011253078 A | 12/2011 |
| WO | WO01006232 A2 | 1/2001 |
| WO | WO 02/084238 A2 | 10/2002 |
| WO | WO 03/067228 A1 | 8/2003 |
| WO | WO03100153 A1 | 12/2003 |
| WO | WO2007078505 A2 | 7/2007 |
| WO | WO 2009/141622 A1 | 11/2009 |
| WO | 2014089120 | 6/2014 |
| WO | 2015015493 | 2/2015 |
| WO | WO2015050464 A | 4/2015 |

OTHER PUBLICATIONS

U.S. Appl. No. 14/818,986, entitled "Optical Filter and Spectrometer", by Smith et al., filed Aug. 5, 2015, 53 pages.
Xin et al., "A vectored water jet propulsion method for autonomous underwater vehicles", Ocean Engineering, Vol. 74, Nov. 2013, 8 pages, XP028778880.
Extended European Search Report corresponding to EP 16 18 2511, dated Apr. 3, 2017, 13 pages.
PCT/US2015/013415 Search Report dated Mar. 30, 2015, 2 pages.
Extended European Search Report corresponding to EP 15 74 3537, dated Aug. 7, 2017, 9 pages.
Extended European Search Report corresponding to EP 16 18 2550, dated Apr. 13, 2017, 15 pages.
BMG Labtech the Microplate Reader Company, "CLARIOstar® High Performance Microplate reader with Advanced LVF Monochromators™", Aug. 2013, 8 pages.
Partial European Search Report corresponding to EP 16 18 2550, dated Jan. 2, 2017, 8 pages.

* cited by examiner

IN-SITU SPECTRAL PROCESS MONITORING

BACKGROUND

Manufacturing processes used in the preparation of pharmaceuticals, food, distillates and chemical compounds may include some type of sensor inspection of the mixing process, for example, spectral, pH, and thermal interrogation. These sensors are typically attached to a wall of a processing vessel, and monitor parameters of the process using a probe protruding into the manufacturing process. However, the stationary nature of sensors having a fixed position limits inspection capabilities to the product in the immediate vicinity of the sensor's fixed position and may not provide information about other parts of the process.

A collimating element may be required prior to variable optical filters to prevent the spectral selectivity of the linearly variable filter from being degraded. Degradation may happen because the optical filter may include a stack of thin dielectric films, and the wavelength-selective properties of thin film filters are generally dependent on the angle of incidence of incoming light, which may deteriorate spectral selectivity and wavelength accuracy of thin film filters. However, for the device in the present disclosure it may be beneficial to reduce the size of the spectrometer even more by eliminating bulky lenses.

DETAILED DESCRIPTION

Figure 1:
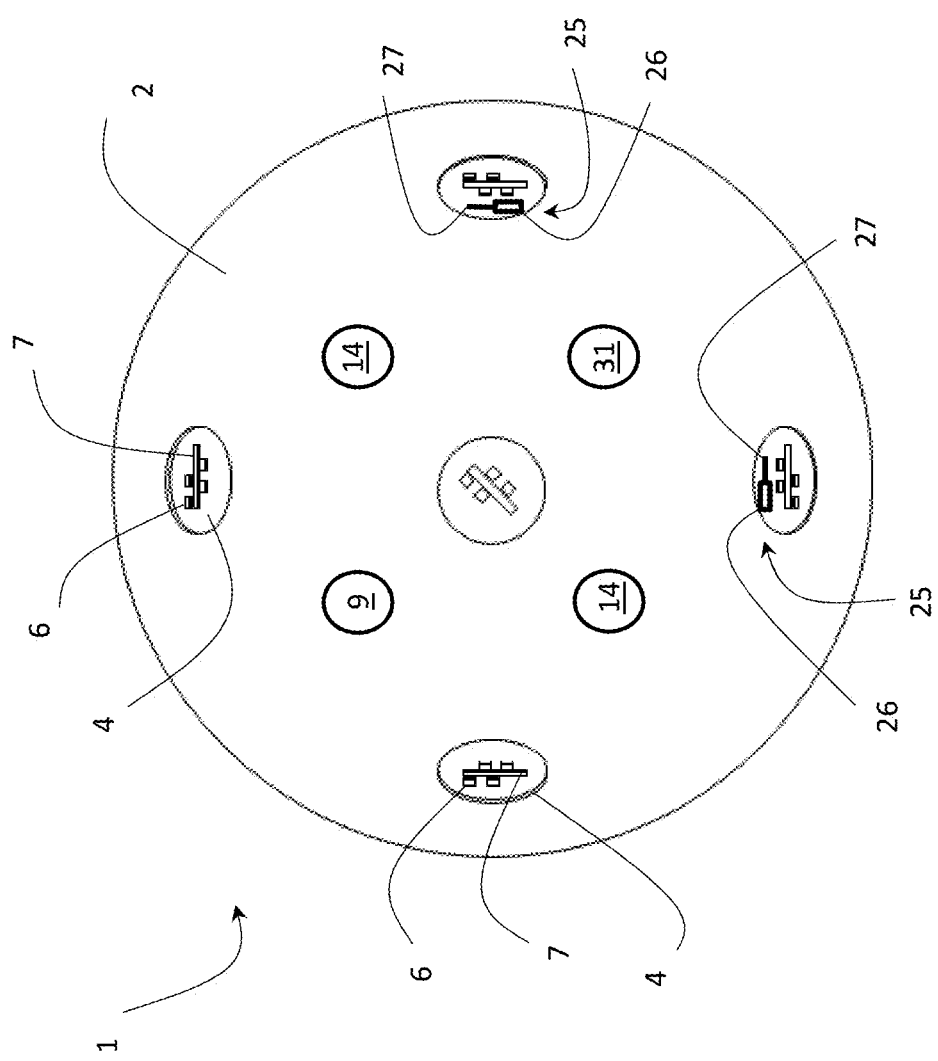
FIG. 1 is a diagram of a top view of a probe.
Figure 2:
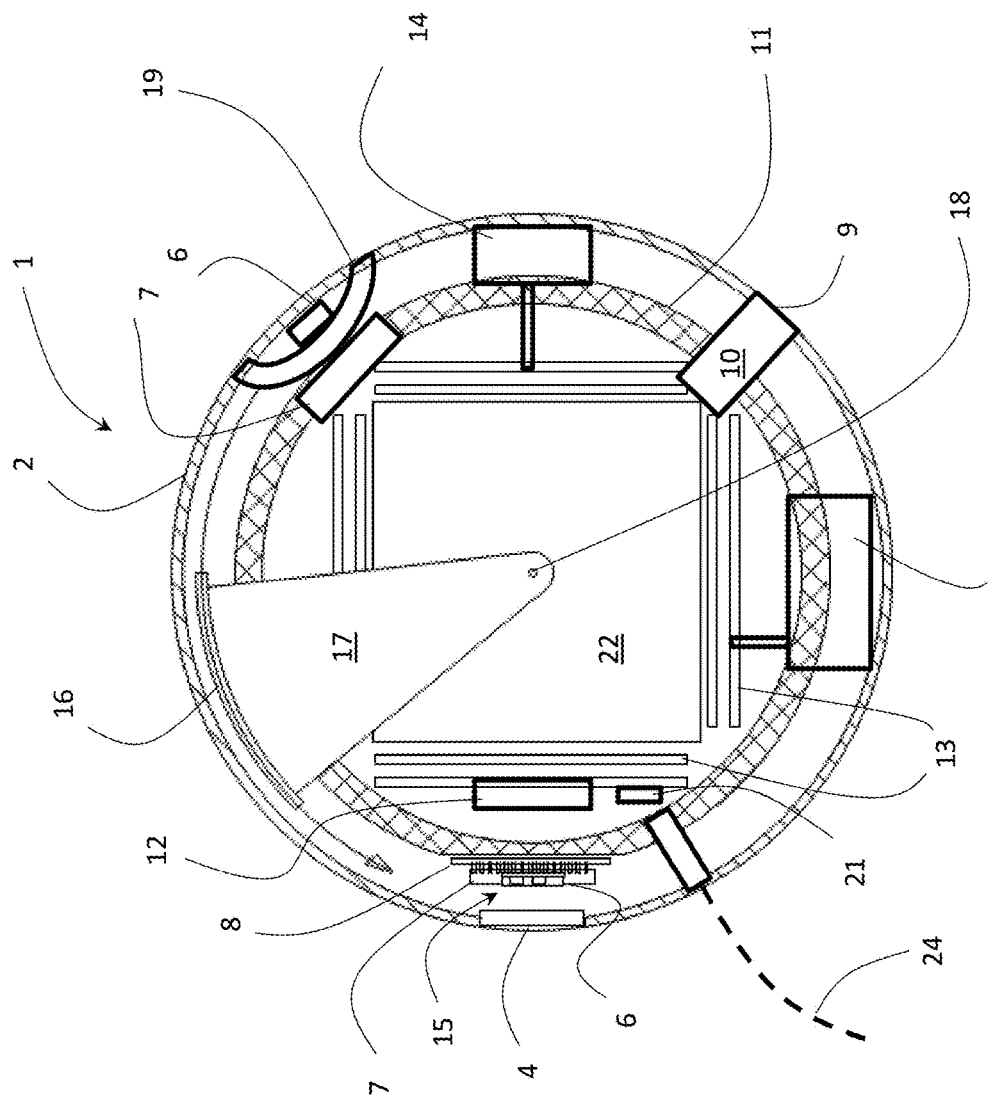
FIG. 2 is a diagram of a cross-sectional view of the probe of FIG. 1.
Figure 3A:
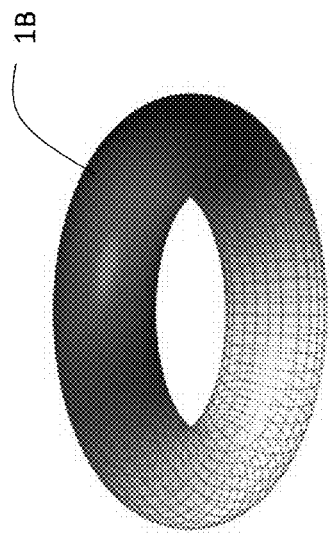
FIGS. 3a to 3d are diagrams of alternative shapes for the probe of FIG. 1.
Figure 3B:
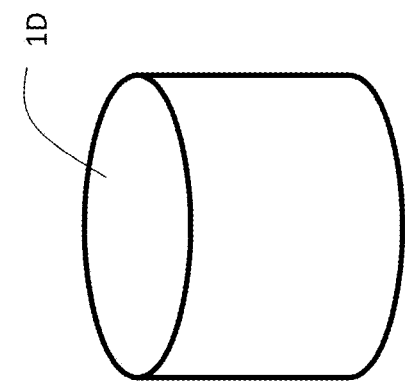
Figure 3C:
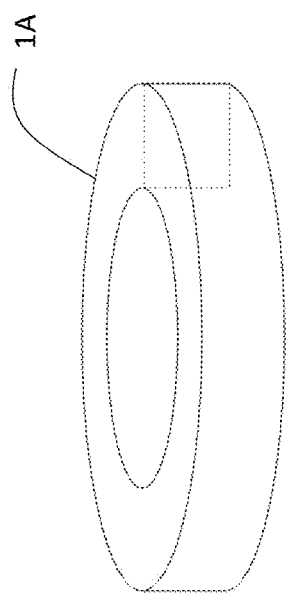
Figure 3D:
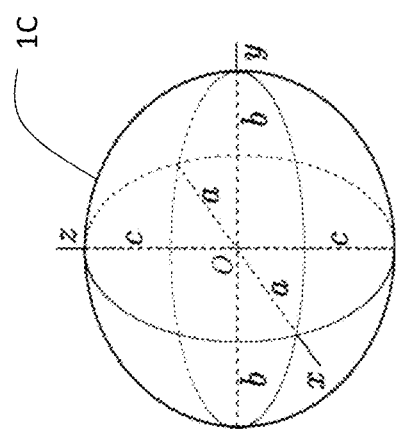

Spectral evaluation at various times and locations in a flowing material, such as liquids, powders and gas, provides powerful process monitoring capabilities. FIG. 1 is a diagram of a top view, and FIG. 2 is a diagram of a cross-sectional view of a probe 1 according to an example implementation described below. The probe 1 may be a spatially variable filter (SVF) based spectral probe and includes an outer housing 2, which may be monolithic or multi-sectional in form and may be hermetically sealed, thereby making the probe 1 robust for applications in which it is immersed in a material the probe is to measure. The outer housing 2 may take one of several shapes or combinations thereof including, but not limited to, spherical 1 (FIGS. 1 and 2), toroidal 1A (FIG. 3A), rounded toroidal 1B (FIG. 3B), ellipsoid or prolate spheroid (football) 1C (FIG. 3C), and cylindrical 1D (FIG. 3D) depending on the application. In one example implementation, the outer housing 2 may be made of or include a corrosion-resistant material, such as stainless steel or a polymer material.

The outer housing 2 may include one or more windows 4 spaced apart on the outer housing 2 or the outer housing 2 may be entirely transparent, i.e. a continuous window. In various example implementations, the outer housing 2 may include any of 1 to 20 or more windows 4. The one or more windows 4 enable light reflected or refracted from the surrounding material to be captured by a corresponding linearly or spatially variable optical filter (SVF) 7 inside the probe 1. The reflected or refracted light may originate from one or more internal light sources 6, an external light source (not shown), ambient light, or a combination thereof. The SVF 7 may be discrete or continuously varying. The filter 7 may be based on other dispersive elements, e.g. gratings, or prisms, or may be based on other technology, such as MEMS, dyes and pigments, FTIR, and Raman. The SVF 7 separates the captured light into a spectrum of constituent wavelength signals for analysis.

The windows 4 may be made of any suitable material, which is optically transparent for the desired transmission and reflected or refracted wavelengths, e.g., sapphire, silicon, Teflon, glass, etc. The internal light source 6 may be any suitable light source, e.g., a tungsten or LED light source, for transmitting the required wavelength band of light, e.g., visible (350 nm to 900 nm) and/or near infrared (NIR). In an example implementation, for near infrared, the light source 6 may be comprised of one or more onboard incandescent lamps, e.g. vacuum tungsten lamps, that provide broadband illumination, e.g., over 500 nm, over 700 nm, or over 1000 nm across the active range of the instrument, e.g., for the NIR in the 900 nm to 1700 nm range or in the 900 nm to 2150 nm range. One lamp 6 is sufficient; however, two lamps provides more light for the sample to interact with, hence shorter integration times.

In an example implementation, as illustrated in FIG. 2, a conduit 19 extending from an opening in the outer housing 2 into the outer housing 2 to an outlet in the outer housing 2 may be provided enabling the passing of the flowing material, e.g. liquid, in between the light source 6 and the SVF 7 within the outer housing 2 for generating a transmission spectrum via the photodetectors 8 and the controller 12. The entire conduit 19 may be transparent to the transmitted light providing the necessary window for light to be transmitted from the light source 6 to the SVF 7, or one or more sections of the conduit 19 may be transparent providing the required window(s) for transmitted, refracted or reflected light.

Mounted beneath each SVF 7 is an array of photodetectors 8 forming a spectrometer 15 and generating a power reading for each constituent wavelength signal, thereby providing a spectrum of the reflected light. Each of the spectrometers 15 in each probe 1 may have a same spectral range or different spectrometers 15 may have different spectral ranges, e.g., overlapping or adjacent, to enable a broad spectral range to be stitched together from the individual spectrometers 15. Another example implementation may include a plurality of fiber bundles, each connecting to a single spectrometer 15 for light supply and data collection. Each bundle may communicate with a different window 4, and may be sequentially coupled to the single spectrometer 15.

The photodetectors 8 may be a broadband detector array, e.g. more than 500 nm, more than 600 nm, or more than 700 nm wide, such as an indium gallium arsenide (InGaAs) detector covering 950 nm to 1650 nm, which may be extended to 1150 nm to 2150 nm, if desired or required. For multiple spectrometer probes 1 and multiple probe systems, different spectrometers 15 within each probe 1 and different probes 1 within each system may have light sources 6, filters 7 and photodetectors 8 with different spectral ranges to cover a wider spectrum, e.g. ultraviolet to infrared, to enable a broad range of tests.

An inner frame 11 may be mounted inside the outer housing 2 for supporting all of the SVF's 7 and photodetector arrays 8. The inner frame 11 may be made of or include one or more of a printed circuit board material, plastic, metal, ceramic, or other suitable material. A controller 12 may be mounted within or on the inner frame 11. The controller 12 may comprise suitable hardware, e.g., processor and memory chips mounted on printed circuit boards 13, along with suitable software for controlling all of the probes features, including spectrum generation, storing, and analysis, thereby providing a self-contained spectral probe 1 for immersion in the material, in particular when the material is moving or flowing in production.

Other types of sensors 14 that may be included within the probe 1 include, but are not limited to, pH sensors, temperature sensors, pressure sensors, voltage sensors, velocity sensors, accelerometers, gyroscopes, and onboard cameras and forward looking infrared (FUR) sensors. In various example implementations, the probe 1 may include multiple similar and/or different sensors positioned around the outer housing 2 of the probe 1. These multiple sensors 14 can enable multiple data sets to be interrogated and improve the quality of the various measurements. Each of the sensors 14 along with the photodetector arrays 8 are connected to the controller 12 for control and data storage.

Each probe 1 may include one or more shutters 16 within the outer housing 2, presenting calibration standards that moves into and out of location in front of each spectrometer 15 as part of a calibration process. In the example implementation illustrated in FIG. 2, the shutter 16 is mounted on the end of a rotating arm 17, which rotates about a central anchor 18 connected to the inner frame 11. The shutter 16 may recalibrate each spectrometer 15 after a predetermined time, e.g., at least every 5 minutes of operation, or after a predetermined number of uses, e.g., at least after every 300 spectral readings.

The shutter 16 includes a calibrated reflectance standard to be rotated between the light source 6 and the window 4 to reflect the light from each light source 6 directly to the corresponding SVF 7. The reflectance from this known standard is then compared to previous tests to determine any change in illumination inside the probe 1.

Figure 7:
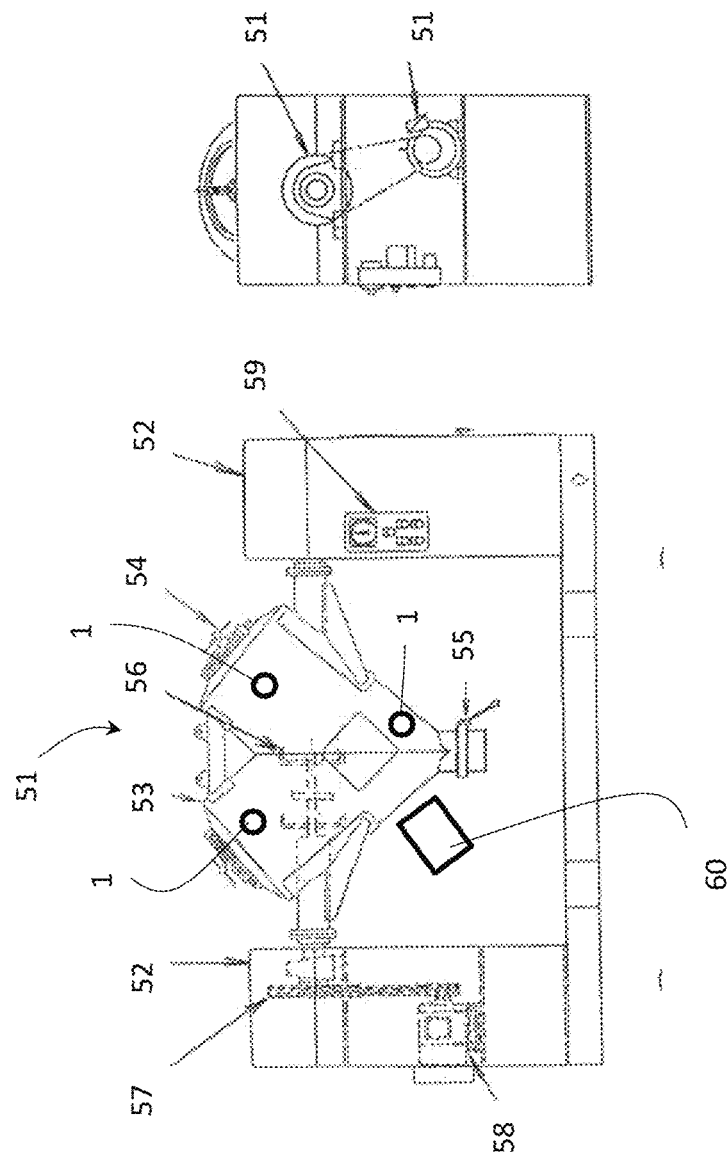
FIGS. 7a and 7b is a diagram of side and end views, respectively, of a V-shaped mixing vessel for use with the probe of FIGS. 1 to 4.
Figure 8:
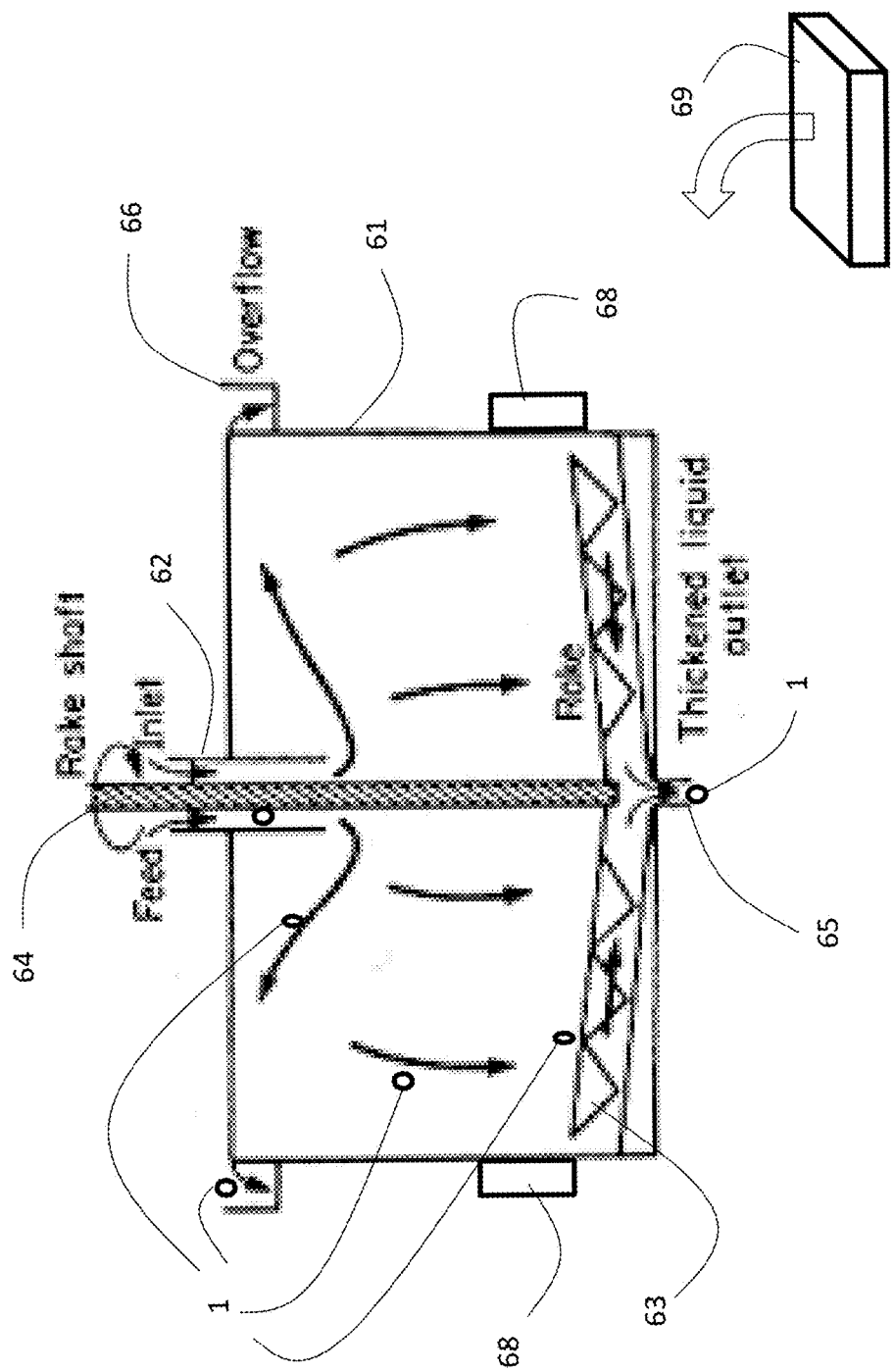
FIG. 8 is a diagram of a settling tank for use with the probes of FIGS. 1 to 4.
Figure 9:
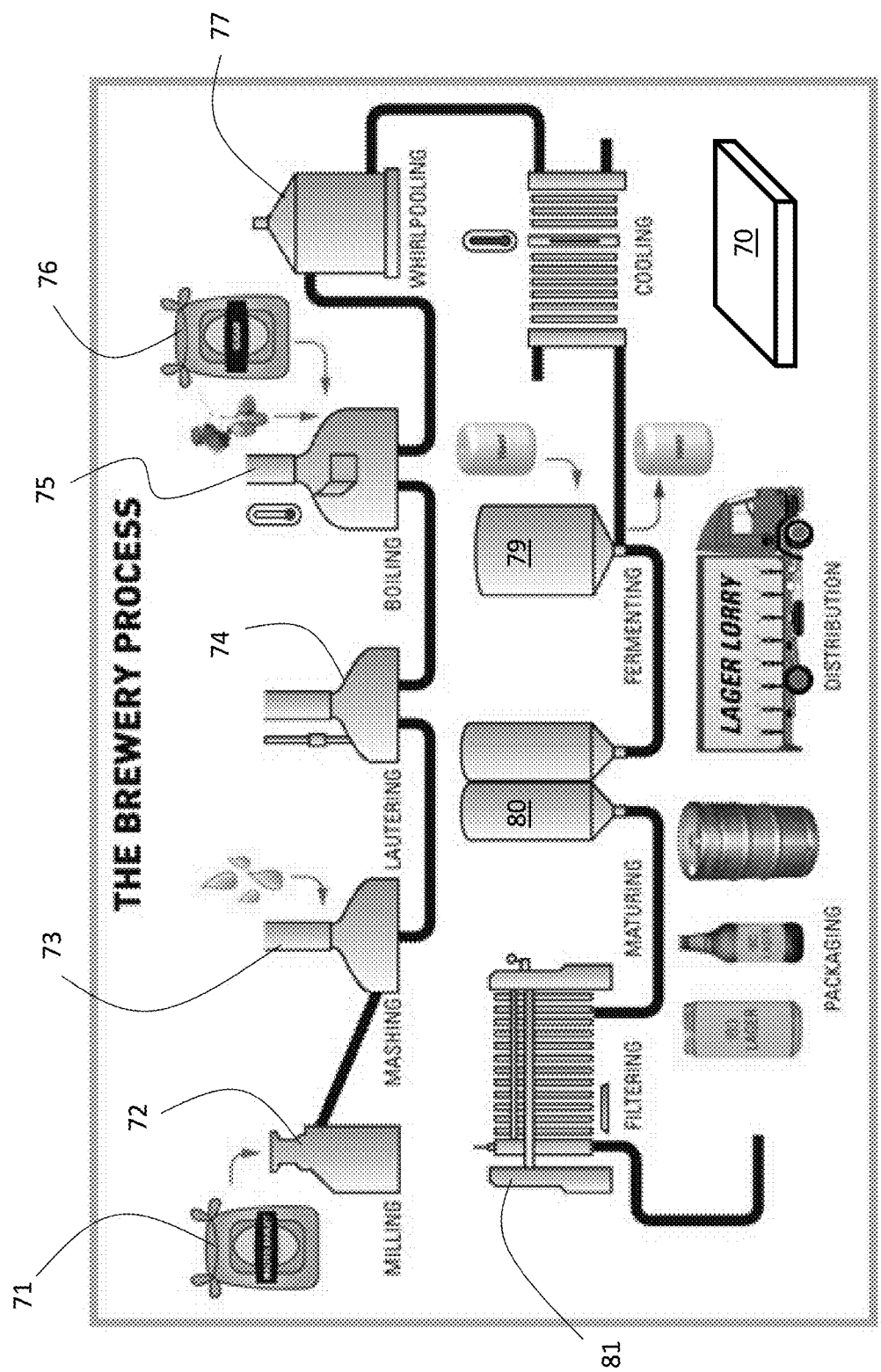
FIG. 9 is a diagram of a process for use with the probes of FIGS. 1 to 4.

A communication module 21 is provided to enable control and/or data signals to be sent between the controller 12 and a base station (shown in FIGS. 7 to 9). In an example implementation, the base station may be monitored by process monitoring engineers. In another example implementation, the base station may include an automated process control system. The communication module 21 may be one or more of a wireless transceiver, a tethered communication cable connection, a photo transceiver, or an acoustical transceiver. A communication module 21 that is wireless may require antennas (not shown) positioned within or outside the outer housing 2 to achieve a real-time data transfer connection with the base station.

The probe 1 may be self-powered with the use of replaceable of rechargeable batteries 22 and/or may be powered by a tethered power cable 24 adjacent to or coordinated with the optional communication cable connection (not shown). The power cable 24 may act as a communication line interconnecting the communication module 21 with the base station, and a tether for retrieving the probe 1 from the flowing media. Since the outer housing 2 may be hermetic, in an example implementation, the batteries 22 may be recharged using an induction connection. In an example implementation, the controller circuit 12 may employ the use of a position system tracker (not shown), e.g., a global positioning system (GPS), to track the location of the probe 1 within the manufacturing or monitoring process. Another possible position tracking system comprises a radio transmitter (not shown) in the probe 1 for signaling an array of fixed directional radio receivers (not shown) positioned around a processing vessel. The array of fixed direction radio receivers may be used to coordinate the position of the probe 1 within the fixed processing vessel or system, whereby the base station and/or each probe's controller 12 may determine the probe's position. An inertial measurement unit (IMU) (not shown) may also be provided to enable the controller 12 or the base station to monitor the probe 1 for orientation and direction of travel within the process vessel.

In one example implementation, the probe 1 may be compatible with the process it is intended to interrogate, for example, the outer housing 2 may be made of IP67 or higher plastic NEMA 4, or the like, for package hermiticity and dust ingress and compatible chemical resistance from the material it is immersed in. In an example implementation, the probe 1 may have variable buoyancy to adjust its buoyancy for use in a liquid process. As stated earlier, the probe 1 may be free to move within the process or may be attached to a fixed object via tether for post process retrieval.

In an example implementation, the outer housing 2 may be ruggedized to handle impacts from mixing or pressurized actions within the manufacture process. In an example implementation, the probe 1 may be used in a process that requires extended monitoring times and the controller 12 may include programming to instruct the photodetector arrays 8 and sensors 14 to change into low power "Stand by" modes to conserve power during long process cycles.

Figure 4:
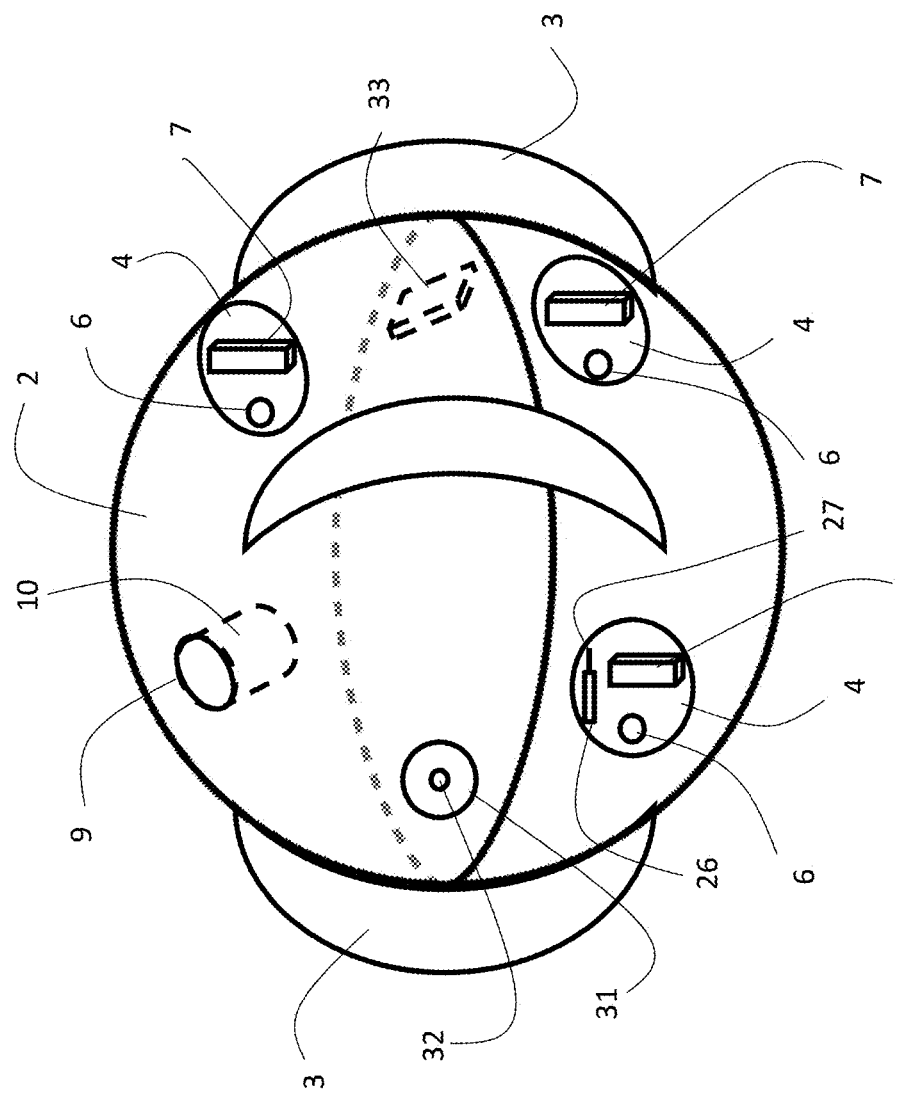
FIG. 4 is a diagram of an isometric view of the probe of FIGS. 1 and 2.

FIG. 4 is a diagram of an isometric view of a probe 1 according to an example implantation described below. The outer housing 2 of the probe 1 may include structural features that facilitate movement and stability with and through the material in which the probe is immersed. The structural features may include, for example, dimples, small or large ribs, stubs, semi-circular or rectangular ribs, veins, or fingers. The example implementation probe 1 in FIG. 4 includes a number of ribs 3. The structural features may provide protection for the probe 1 from contact with other objects, e.g., vessel walls. The structural features may also provide enhanced mixing and/or reduced clumping within the flowing material as the probe 1 travels through the flowing material. The structural features may also help in maintaining orientation of the probe 1 relative to the direction of the flow of the material in which the probe 1 is immersed, facilitate heat exchange with the material, and direct the material to be measured in front of the sensor windows 4 for measurement and for removing debris that may have become adhered thereto.

The outer housing 2 may also include a hatch 9 for accessing a storage compartment 10. The hatch 9 may be opened by the controller 12 in response to a signal from the base station or in response to an internal signal from the controller 12, e.g., a spectrum reading or other test signal reaching a predetermined or desired level. In an example implementation, the storage compartment 10 may contain a substance used to facilitate a chemical process, e.g., a catalyst. In an example implementation, the storage compartment 10 may contain a substance used to mark a specific location, e.g., a dye. In an example implementation, the storage compartment 10 may contain a substance used to alter the chemical parameters of the substance in which the probe 1 is immersed, e.g., pH or toxicity. Alternatively, the hatch 9 may be opened in response to a signal from the controller 12 and/or the base station to capture fluid from the material in which the probe is immersed in the storage compartment 10 for further testing or for controlling buoyancy of the probe 1.

The probe 1 may also include a separate buoyancy system 31, which will enable the buoyancy of each probe 1 to be individually adjusted before insertion into the flowing material or during active monitoring in the flowing material to enable the probe 1 to be guided or propelled to a different location, and different depths within the flowing material. The buoyancy system 31 may comprise a fluid expelling device for expelling fluid from a storage tank or bladder 32, thereby decreasing the density of the probe 1 and/or a fluid intake device for capturing surrounding fluid, thereby increasing the density of the probe 1.

The probe 1 may also include a propulsion system 33, which will enable the position of each probe 1 to be adjusted by the controller 12 and/or the base station. The propulsion system 33 may include the release of a pressurized burst of fluid stored in a storage tank, an electro-magnet, which may be energized to attract the probe 1 towards a metallic structure in the processing tank, or a propeller.

In certain applications, a window cleaner system 25, which may be controlled by the controller 12, may be provided to periodically wipe or remove accumulated material off of the exterior of the windows 4. The cleaner system 25 may comprise an external concentric shell (not shown) with a wiper system mounted on the outer housing 1. The wiper system may include a wiper 26 mounted on an a rotating or translating arm 27 which may be swept across the windows 4. Alternatively or in addition to the wiper system, the propulsion system 33 may spin the probe 1 at high speed within the volume of flowing material to throw off any accumulated material on the windows 4 by centrifugal force. Other cleaning systems may include one or more of a sonic agitator to provide sonic agitation to clear the windows 4, a heater to heat the windows 4 and to drive off moist powders, and a source of electricity to generate an electric discharge.

Figure 5:
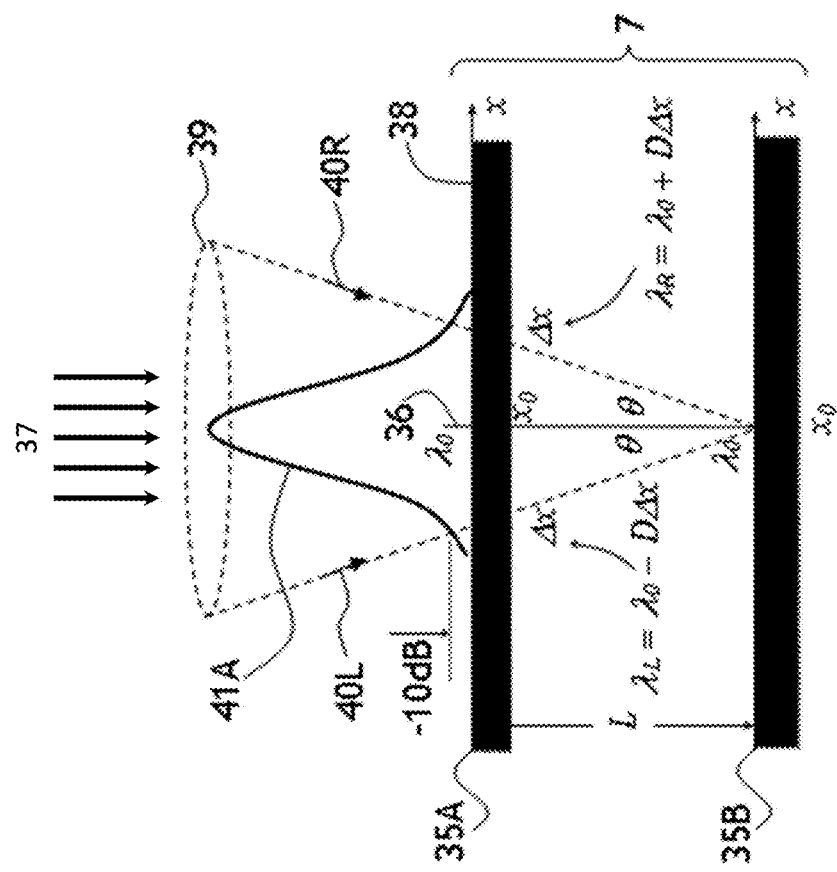
FIG. 5 is a diagram of a side view of a dual SVF filter.
Figure 6:
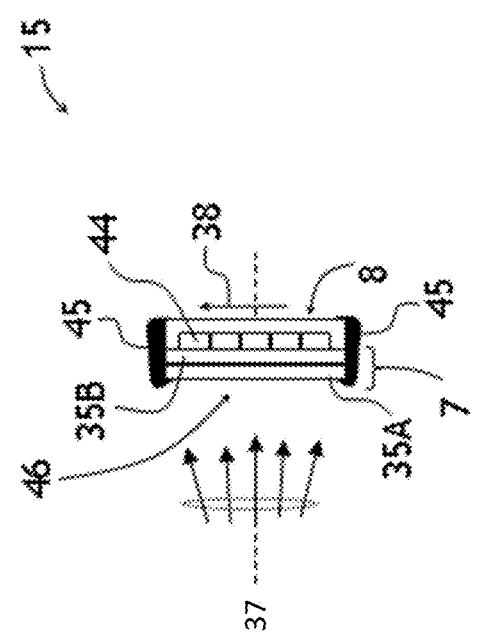
FIG. 6 is a diagram of a side view of a spectrometer.

FIG. 5 is a diagram of a side view of a dual SVF filter according to an example implementation described below. FIG. 6 is a diagram of a side view of a spectrometer according to an example implementation described below. The spatially variable filter (SVF) 7 comprises a center wavelength of a passband varying, e.g. linearly or non-linearly, along an x-axis, and in some embodiments in the y-axis forming a 2D spatially variable filter (SVF).

Accordingly, the SVF 7 may include sequentially disposed upstream 35A and downstream 35B spatially variable bandpass optical filters (SVF) separated by a predetermined fixed distance L in an optical path 36 of an optical beam 37, as disclosed in U.S. patent application Ser. Nos. 14/608,356 and 14/818,986, entitled "OPTICAL FILTER AND SPECTROMETER" by Smith et al, filed Aug. 5, 2015, which are herein incorporated by reference. The upstream SVF 35A and the downstream SVF 35B each have a bandpass center wavelength $\lambda_T$ varying in a mutually coordinated fashion along a common first direction 38 represented by the x-axes. The first direction 38 is transversal to the optical path 36. By way of a non-limiting example, the bandpass center wavelength $\lambda_T$ of both the upstream 35A and downstream 35B SVF have respective monotonic, linear dependences. The configuration of the optical filter 7 enables a dependence of spectral selectivity of the optical filter 7 on a degree of collimation of the optical beam 37 to be lessened as compared to a corresponding dependence of spectral selectivity of the downstream SVF 35B on the degree of collimation of the optical beam 37.

In the example of FIG. 5, the upstream 35A and downstream 35B SVF are aligned with each other, so that the reference point $x_0$ corresponding to the reference bandpass center wavelength $\lambda_0$ of the downstream filter 35B is disposed directly under the reference point $x_0$ corresponding to the reference bandpass center wavelength $\lambda_0$ of the upstream filter 35A. The upstream filter 35A functions as a spatial filter for the downstream filter 35B, defining a predetermined or preset angle of acceptance 39 for the downstream filter 35B. The angle of acceptance 39 is limited by left 40L and right 40R marginal rays at the reference wavelength $\lambda_0$, each propagating at the angle θ to a normal 36 to the upstream 35A and downstream 35B filters and striking downstream filter 359 at the same reference point $x_0$. The angle of acceptance 30 may be derived from a passband 41A of the upstream filter 35A as follows.

In the geometry illustrated in FIG. 5, the left marginal ray 40L strikes the upstream filter 35A at a location $x_0$-Δx. Transmission wavelength $\lambda_L$ at that location is, according to Eq. (1), $\lambda_L = \lambda_0 - D\Delta x$. Since the left marginal ray 40L is at the reference wavelength $\lambda_0$, the left marginal ray 40L will be attenuated depending on a selected and predetermined bandwidth of the passband 41A of the upstream SVF 35A; for sake of this example, e.g. a 10 dB bandwidth is taken to be 2DΔx. Thus, the left marginal ray 40L will be attenuated by the predetermined attenuation, e.g. 10 dB. Similarly, the right marginal ray 40R strikes the upstream SVF 35A at a location $\lambda_0 + \Delta x$. Transmission wavelength $\lambda_R$ at that location is, according to Eq. (1), $\lambda_R = \lambda_0 + D\Delta x$. The right marginal ray 40R will also be attenuated by the predetermined attenuation, e.g. 10 dB. All rays at the reference wavelength $\lambda_0$ within the acceptance angle 39 will be attenuated by a value smaller than the predetermined level, e.g. 10 dB; and all rays at the reference wavelength $\lambda_0$ outside the acceptance angle 39 will be attenuated by a value larger than the predetermined level, e.g. 10 dB, thereby greatly reducing the amount of light, at incident angles greater than the acceptance angel 39, from being transmitted to the downstream SVF 35B, thereby eliminated the need for bulky collimating lenses and optics. The upstream SVF 35A functions as spatial filter, effectively limiting the numerical aperture (NA) of incoming light to be separated in individual wavelengths by the downstream SVF 35B. This results in reduction of the dependence of spectral selectivity of the SVF 7 in comparison with the corresponding dependence of the spectral selectivity of the single downstream SVF 35B on the degree of collimation of the optical beam 37. The term "spectral selectivity" may include such parameters as passband width, stray light rejection, extinction ratio, etc.

The center wavelengths $\lambda_T$ of the upstream 35A and downstream 35B SVF may be monotonically increasing or decreasing in the first direction 38. The dependence of the bandpass center wavelength $\lambda_T$ on the x-coordinate along the first direction 38 of the upstream SVF 35A and downstream 35B SVF may be identical, or different to enable adjustment of the acceptance angle and/or wavelength response of the optical filter 7. In one embodiment, the bandpass center wavelengths $\lambda_T$ of the upstream SVF 35A and downstream SVF 35B are aligned with each other, such that a line connecting positions corresponding to a same bandpass center wavelength $\lambda_T$ of the upstream SVF 35A and the downstream SVF 35B forms an angle of less than a predetermined amount, e.g., 30°, with the normal 36 to the downstream SVF 35B. For non-zero angles with the normal 36, the acceptance cone 39 may appear tilted. Thus, it is possible to vary the acceptance cone 39 direction by offsetting the upstream SVF 35A and the downstream SVF 35B relative to each other in the first direction 38. For a better overall throughput, a lateral distance $\Delta x_1$ along the first direction 38, corresponding to a bandwidth of the upstream SVF 35A, may be larger than a corresponding lateral distance $\Delta x_2$ along the first direction 38, corresponding to a bandwidth of the downstream SVF 35B. In one example implementation, the upstream SVF 35A and the downstream 35B SVF each have a 3 dB passband no greater than 10% of a corresponding wavelength range of the upstream SVF 35A and the downstream SVF 35B.

Referring to FIG. 6, the spectrometer 15 includes the optical filter 7 and a photodetector array 8 disposed in the optical path downstream of the downstream SVF 35B. The photodetector array 8 may include pixels 44 disposed along the first direction 38 and optionally along a second perpendicular direction (into the page) for detecting optical power levels of individual spectral components of the optical beam, e.g., reflected by the flowing material from the light source 6. In an example implementation, the photodetector array may be the 2D photodetector array disclosed in U.S. patent application Ser. No. 14/818,986, entitled "OPTICAL FILTER AND SPECTROMETER" by Smith et al, filed Aug. 5, 2015, which is incorporated herein by reference. Accordingly, the optical beam may be converging, diverging, collimated, etc. As explained above, the dual-filter structure of the optical filter 7, including the upstream SVF 35A and the downstream SVF 35B results in lessening the dependence of spectral selectivity of the optical filter 7 on a degree of collimation of the returning light.

In one example implementation, the photodetector array 8 may be in direct contact with the downstream SVF 35B. The photodetector array 8 may be flooded with a potting material so as to form an encapsulation 45. One function of the encapsulation 45 is to insulate the photodetector array 8, while not obscuring a clear aperture 46 of the downstream SVF 35B of the optical filter 7. Another function of the encapsulation 45 is to protect edges of the upstream 35A and downstream 35B filters from impact, moisture, etc.

Applications

FIGS. 7a and 7b are diagrams of side and end views, respectively, of a V-shaped mixing vessel for use with the probes 1. With reference to FIGS. 7a and 7b, a plurality of the probes 1 may be used in a monitoring system for a batch processing system, e.g., in the pharmaceutical industry. A processing tank 51 includes a support frame 52 for supporting a mixing vessel, such as V-shaped mixing vessel 53. The mixing vessel 53 includes at least one input port 54 for inputting the raw ingredients, and at least one output port 55 for discharging the finished product. An agitator or chopper 56 may be provided inside the mixing vessel 53 to reduce the size of the raw ingredients and/or mix the various raw ingredients together. The agitator 56 may be rotated using a sprocket and chain structure 57, or some other suitable driving assembly, which is driven by a motor 58. A control system 59 may be provided for controlling the input of the ingredients, the activation and speed of the agitator 56, as well as the timing of the discharge of the finished product via output port 55. The control system 59 may be controlled automatically according to pre-set programming stored on non-transitory memory actuated by a computer controller or may require human intervention at selected times.

One or more probes 1 may be placed in with the raw ingredients, or even separately with different raw ingredients that are input through separate input ports 54, and follow along with the raw ingredients as they mix with each other and/or react with each other due to their chemical properties or other external factors, such as a change in temperature or pressure, or the addition of a catalyst. Throughout the process, the probes 1, via the controller 12 and the communication module 21 may continually transmit spectrum data to the control system 59 (base station), e.g., wirelessly via WIFI, at predetermined time intervals to provide constant status updates of the chemical process. The control system 59 and/or the controller 12 may utilize the spectrum data and any other test data collected by the other sensors 14 in one of many different ways. In one example implementation, the control system 59 and/or the controller 12 may utilize the spectrum and test data to determine when the process is complete, i.e. to shut the process off, and output the finished product. In addition, the control system 59 and/or the controller 12 may utilize the spectrum and test data to adjust the frequency or speed of the agitator 56 and/or to adjust the parameters of the chemical process, e.g. adjust any one or more of the temperature, the pressure, and the amount of catalyst. For multi-step processes, the control system 59 and/or the controller 12 may utilize the spectrum and test data to initiate subsequent steps in the process, e.g. as the spectrum and test data reach desired output levels. The control system 59 and/or the controller 12 may even distribute additional catalysts or ingredients at specific times based on the spectrum and test data from the storage compartment 10 via hatch 9.

The control system 59 and/or the controller 12 may identify the position of the various probes 1 using each probe's positioning system, e.g., GPS, and may prioritize which probe 1 has greater significance in determining a next step based on the position of that probe 1. In addition, since each probe 1 may have a plurality of spectrometers 15, the control system 59 and/or the controller 12 may average the spectrum data for each probe 1. The averaging process may include eliminating high and low measurements or any measurement outside a predetermined deviation from the average of the remaining measurements. Averaging may include averaging the different spectra from the different windows 4/spectrometers 15 within each probe 1, and/or average the spectra from multiple probes 1 at multiple locations throughout the volume of flowing material. The controller 12 or the control system 59 may also include suitable programming to perform other spectrum processing including differencing similar or different spectra regions to compare readings or combining different overlapping or adjacent spectra to generate a wider spectrum.

The position of each probe 1 may be adjusted by utilizing the onboard propulsion system 33, the onboard buoyancy system 31, or by using a process propulsion system external to each probe 1, such as an electro-magnet 60 energized at a predetermined or desired location to attract one or more of the probes 1 in a required direction or into a desired zone of the vessel 53. In this system, the probes 1 can easily be collected for re-use when the finished product is output the outlet port 55.

With reference to FIG. 8, the probes 1 may be used in a continuous process including a settling tank 61. The settling tank 61 includes an input port 62 for inputting raw or unprocessed ingredients proximate the middle of the tank 61, and an agitator or rake 63, which is mounted on the end of rotating shaft 64, and rotates around the bottom of the settling tank 61. An output port 65 is provided in the bottom of the settling tank 61 for outputting processed material, e.g. thickened liquid. An overflow channel 66 is provided around the top of the settling tank 61 to capture all the lighter fluid and materials, which rise to the top of the settling tank 61.

One or more probes 1 may be placed in with the raw ingredients through input port 62, and follow along with the raw ingredients as they mix with each other and/or react with each other due to their chemical properties or other external factors, such as a change in temperature or pressure, or the addition of a catalyst. Throughout the process, the controllers 12 may continually transmit spectrum data, e.g., wirelessly via WIFI, to a base station 69 at predetermined time intervals to provide constant status updates of the chemical process. The base station 69 and/or the controllers 12 may utilize the spectrum data and any other test data collected by the other sensors 14 in one of many different ways. For example, the base station 69 and/or the controllers 12 may simply utilize the spectrum and test data to determine when the process has reached a certain stage, i.e., outputs the finished product via the output port 65. In addition, the base station 69 and/or the controllers 12 may utilize the spectrum and test data to adjust the frequency or speed of the rake 64 and/or to adjust the parameters of the chemical process, e.g. adjust any one or more of the temperature, the pressure, and the amount of catalyst. For multi-step processes, the base station 69 and/or the controllers 12 may utilize the spectrum and test data to initiate subsequent steps in the process, e.g., as the spectrum and test data reach desired output levels. The controllers 12 and/or the base station 69 may even distribute additional catalyst or ingredients at specific times based on the spectrum and test data from the storage compartment 10 via hatch 9.

The base station 69 and/or the controllers 12 may identify the position of the various probes 1 using each probes positioning system, e.g., GPS, and may prioritize which probe 1 has greater significance in determining a next step based on the position. In addition, since each probe 1 may have a plurality of spectrometers 15, the base station 69 and/or the controllers 12 may average the spectrum data for each probe 1. The averaging process may include eliminating high and low measurements or any measurement outside a predetermined deviation from the average of the remaining measurements.

The position of each probe 1 may be adjusted by the controllers 12 and/or the base station 69 utilizing the onboard propulsion system 33, the onboard buoyancy system 31 or by using a process propulsion system external to each probe 1, such as an electro-magnet 68 energized at a predetermined or desired location to attract one or more of the probes 1 in a required direction or into a desired zone of the settling tank 61. In this system, the probes 1 may have different buoyancy properties, e.g. one for settling to the bottom for output the output port 65 and one for rising to the top for output the overflow channel 66. Accordingly, the probes 1 can easily be collected for re-use when the finished product is output the various ports 65 and 66.

With reference to FIG. 9, a multi-step process, such as a brewing process, may include several steps, e.g. lautering, boiling, fermenting, conditioning, filtering, and packaging, which may require precision monitoring provided by a monitoring system including a base station 70 and a plurality of probes 1 communicating via a wireless network, e.g., WIFI. The probes 1 may be inserted into each processing tank at each step or the probes 1 may travel with the ingredients through various steps and processing vessels.

Malting is the process where barley grain 71 is made ready for brewing. When malting is complete, the grains 71 are milled or crushed in a mill 72 to break apart the kernels and expose the cotyledon, which contains the majority of the carbohydrates and sugars.

Mashing converts the starches released during the malting stage into sugars that can be fermented. The milled grain is mixed with hot water in a large vessel known as a mash tun 73. In this vessel, the grain and water are mixed together to create a cereal mash. During the mash, naturally occurring enzymes present in the malt convert the starches (long chain carbohydrates) in the grain into smaller molecules or simple sugars (mono-, di-, and tri-saccharides). This "conversion" is called saccharification. The result of the mashing process is a sugar rich liquid or "wort", which is then strained through the bottom of the mash tun 73 or in a separate tank 74 in a process known as lautering. The probes 1 may be deposited into the mash tun 73 to monitor the concentration of enzymes and the concentration of starches in the wort. Prior to lautering, the mash temperature may be raised to about 75-78° C. (167-172° F.) (known as a mashout) to deactivate enzymes. Probes 1 may be used near the bottom of the mash tun 73 or lautering tank 74 to ensure the temperature is within the desired range throughout the container using a temperature sensor 14, and to ensure the concentration of enzymes is reduced to a desired or acceptable level using one of the probe spectrometers. Additional water may be sprinkled on the grains to extract additional sugars in a process known as sparging.

The wort is moved into a large tank 75 known as a "copper" or kettle where it is boiled with hops and sometimes other ingredients 76, such as herbs or sugars. This stage is where many chemical and technical reactions take place, and where important decisions about the flavor, color, and aroma of the beer are made. The boiling process serves to terminate enzymatic processes, precipitate proteins, isomerize hop resins, and concentrate and sterilize the wort. Hops add flavor, aroma and bitterness to the beer. The spectrum signals from the probes 1 may be used to determine the concentrations of the various elements and the color of the wort At the end of the boil, the hopped wort settles to clarify in a vessel called a "whirlpool" 77, where the more solid particles in the wort are separated out.

After the whirlpool 77, the wort is rapidly cooled via a heat exchanger 78 to a temperature where yeast can be added. The heat exchanger 78 is comprised of tubing inside a tub of cold water. It is very important to quickly cool the wort to a level where yeast can be added safely as yeast is unable to grow in high temperatures. Accordingly, temperature sensors 14 on the probes 1 may quickly determine when the wort has cooled to the required temperature evenly throughout the heat exchanger 78. After the wort goes through the heat exchanger 78, the cooled wort goes into a fermentation tank 79. A type of yeast is selected and added, or "pitched", to the fermentation tank 79. When the yeast is added to the wort, the fermenting process begins, where the sugars turn into alcohol, carbon dioxide and other components. In the fermentation tank 79, the probes 1 provide spectral signals relating to the concentration of those elements. When the fermentation is complete the brewer may rack the beer into a new tank, called a conditioning tank 80. Conditioning of the beer is the process in which the beer ages, the flavor becomes smoother, and flavors that are unwanted dissipate. Here the spectrum signals from the probes 1 provide a clear indication of when the beer has reached its optimum condition, as well as the monitoring of other characteristics, such as pH. After conditioning for a week to several months, the beer may be filtered using a filter 81 and force carbonated for bottling, or fined in the cask.

The probes 1 may also be used in a much larger monitoring system, such as in active rivers, lakes, oceans and other waterways to monitor the concentration of various elements, such as pollutants, e.g. oil spills, along with other contributing factors, for example temperature and pH. The combination of the location and time of detection, and the type(s) of the pollutant detected, may enable determination of the source of pollution, as well as the resultant damage, e.g. changes in water characteristics, downstream.

As the size of the probes 1 decrease, they may also be used for monitoring humans or other animals in-vivo. In particular, a probe 1 may be ingested and the spectral data may be transmitted to a doctor's base station as the probe 1 traverses the patient's digestive system to monitor content, pH, temperature and various other characteristics.

In an example implementation, the probes 1 may be dropped from some form of flying machine, e.g., airplane, balloon, helicopter or spacecraft, to monitor various atmospheric characteristics, e.g., ozone, allergens, pollutants.

The present disclosure is not to be limited in scope by the specific example implementations described herein. Indeed, other implementations and modifications, in addition to those described herein, will be apparent to those of ordinary skill in the art from the foregoing description and accompanying drawings. Thus, such other implementation and modifications are intended to fall within the scope of the present disclosure. Further, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

We claim:

1. A probe, comprising:
   a hermetically sealed outer housing;
   a light source for transmitting light onto a material;
   a window in the hermetically sealed outer housing,
      wherein the window is optically transparent at one or more of transmitted, refracted or reflected wavelengths of light from the material;
   an optical filter for capturing light transmitted, refracted or reflected from the material, and for separating the captured light into a spectrum of constituent wavelength signals,
      the optical filter comprising:
         an upstream spatially variable bandpass optical filter; and
         a downstream spatially variable bandpass optical filter that is disposed downstream of the upstream spatially variable bandpass optical filter and separated from the upstream spatially variable bandpass optical filter by a distance along an optical path of the captured light; and
   a detector array for providing power readings,
      each power reading, of the power readings, being for a constituent wavelength signal of a plurality of the constituent wavelength signals.

2. The probe according to claim 1,
   wherein the upstream spatially variable bandpass optical filter has a bandpass center wavelength that varies in a mutually coordinated fashion along at least a common first direction transversal to the optical path, and
   wherein light, at the bandpass center wavelength along the upstream spatially variable bandpass optical filter, outside a predetermined acceptance angle is attenuated by more than light inside the predetermined acceptance angle.

3. The probe according to claim 1, wherein the hermetically sealed outer housing comprises a shape that is one of spherical, cylindrical, prolate spheroid, ellipsoid, or toroidal.

4. The probe according to claim 1, wherein the hermetically sealed outer housing comprises structural features arranged on an outside of the hermetically sealed outer housing.

5. The probe according to claim 4, wherein the structural features include one or more of dimples, stubs, semi-circular or rectangular ribs, veins, or fingers.

6. The probe according to claim 1, further comprising:
   a controller for storing the power readings; and
   a communication device for transmitting the power readings to a remote base station.

7. The probe according to claim 6, wherein the communication device is a wireless communication device.

8. The probe according to claim 6,
   wherein the communication device is a wired communication device, and
   wherein the hermetically sealed outer housing is tethered to a structure.

9. The probe according to claim 1, further comprising:
   a positioning system tracker for determining an exact position or orientation of the probe.

10. The probe according to claim 1, further comprising:
    a propulsion system for propelling the probe when immersed in the material.

11. The probe according to claim 1, further comprising:
    a buoyancy adjusting system for adjusting a buoyancy of the probe when immersed in the material.

12. The probe according to claim 1, further comprising:
    a storage compartment; and
    a hatch on the hermetically sealed outer housing, wherein the hatch is operable to open and close the storage compartment.

13. The probe according to claim 12, further comprising:
    a controller for storing the power readings and signaling the hatch to open and release a substance from the storage compartment when the power readings reach a predetermined level.

14. The probe according to claim 1, further comprising:
    a window cleaner for removing debris from the window.

15. The probe according to claim 1, wherein the light source is mounted inside the hermetically sealed outer housing for transmitting the light through the window onto the material.

16. The probe according to claim 1, wherein the hermetically sealed outer housing comprises a conduit extending therethrough from an opening in the hermetically sealed outer housing to an outlet in the hermetically sealed outer housing in between the light source and the optical filter.

17. The probe according to claim 1, further comprising:
    a plurality of windows spaced apart around the hermetically sealed outer housing;
    a plurality of light sources inside the hermetically sealed outer housing for transmitting the light through the plurality of windows onto the material;
    a plurality of optical filters for capturing light transmitted through, and reflected or refracted from the material, and for separating the captured light into the spectrum of the constituent wavelength signals; and a plurality of detector arrays for providing the power readings.

18. The probe according to claim 17, further comprising:
a controller for storing the power readings and averaging the power readings.

19. The probe according to claim 17, further comprising:
a controller for storing the power readings,
wherein the optical filters include different spectral passbands, and
wherein the controller combines the power readings with different spectral passbands to generate a combined spectrum.

20. The probe according to claim 17, further comprising a shutter moveable within the hermetically sealed outer housing into position between the light source and the optical filter.

21. A system comprising:
a plurality of probes, each probe comprising:
a hermetically sealed outer housing;
a light source for transmitting light onto a material;
a window in the hermetically sealed outer housing, wherein the window is optically transparent at one or more of transmitted, refracted or reflected wavelengths of light from the material;
an optical filter for capturing light transmitted, refracted or reflected from the material, and for separating the captured light into a spectrum of constituent wavelength signals,
the optical filter comprising:
an upstream spatially variable bandpass optical filter; and
a downstream spatially variable bandpass optical filter that is disposed downstream of the upstream spatially variable bandpass optical filter, and
the downstream spatially variable bandpass optical filter being separated from the upstream spatially variable bandpass optical filter by a distance along an optical path of the captured light; and
a detector array for providing power readings,
each power reading, of the power readings, being for a constituent wavelength signal of a plurality of the constituent wavelength signals.

22. The system according to claim 21, wherein parameters for the material are adjusted based on the power readings.

23. A method comprising:
placing a probe into a material;
the probe comprising:
a hermetically sealed outer housing;
a light source for transmitting light onto a material;
a window in the hermetically sealed outer housing, wherein the window is optically transparent at one or more of transmitted, refracted or reflected wavelengths of light from the material; and
an optical filter for capturing light transmitted, refracted or reflected from the material, and for separating the captured light into a spectrum of constituent wavelength signals,
the optical filter comprising:
an upstream spatially variable bandpass optical filter; and
a downstream spatially variable bandpass optical filter that is disposed downstream of the upstream spatially variable bandpass optical filter, and
the downstream spatially variable bandpass optical filter being separated from the upstream spatially variable bandpass optical filter by a distance along an optical path of the captured light; and
receiving power readings from probes as the probes travel along with the material, wherein the probes include the probe.

24. The method according to claim 23, further comprising:
adjusting parameters of the material based on the power readings.

25. The method according to claim 23, further comprising:
adjusting a position of the probe by activating a propulsion system.

26. The method according to claim 23, further comprising:
releasing a substance from within the probe.

27. The method according to claim 23, further comprising:
capturing a sample of the material.

* * * * *